(12) United States Patent
Larder et al.

(10) Patent No.: US 6,177,435 B1
(45) Date of Patent: *Jan. 23, 2001

(54) THERAPEUTIC COMBINATIONS

(75) Inventors: Brendan Alexander Larder; Sharon Dawn Symons, both of Kent (GB)

(73) Assignee: Glaxo Wellcome Inc., Research Triangle Park, NC (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/825,674

(22) Filed: Mar. 20, 1997

Related U.S. Application Data

(63) Continuation of application No. 08/221,009, filed on Apr. 1, 1994, now abandoned, which is a continuation of application No. PCT/GB93/00980, filed on May 13, 1993.

(30) Foreign Application Priority Data

| Apr. 2, 1993 | (GB) | 9307013 |
| May 2, 1993 | (GB) | 9210256 |
| May 2, 1993 | (GB) | 9210270 |

(51) Int. Cl.⁷ .......................... A61K 31/505; A61K 31/70
(52) U.S. Cl. .............................. 514/274; 514/49; 514/50
(58) Field of Search ................... 514/49, 50, 274

(56) References Cited

U.S. PATENT DOCUMENTS

| 5,756,478 | 5/1998 | Cheng ..................... 514/45 |
| 5,859,021 | 1/1999 | Cameron et al. ............ 514/274 |
| 5,869,461 | 2/1999 | Cheng et al. .............. 514/43 |
| 5,905,082 | 5/1999 | Roberts et al. ............. 514/274 |

FOREIGN PATENT DOCUMENTS

| 0 196 185 | 10/1986 | (EP) . |
| 0196185 * | 10/1986 | (EP) .............. A61K/31/70 |
| 0 217 580 | 4/1987 | (EP) . |
| 0 291 633 | 11/1988 | (EP) . |
| 0 336 466 | 10/1989 | (EP) . |
| 0 382 526 | 8/1990 | (EP) . |
| 0 384 522 | 8/1990 | (EP) . |
| 0 393 604 A2 | 10/1990 | (EP) . |
| 0 462 800 A2 | 12/1991 | (EP) . |
| 0 475 231 A1 | 3/1992 | (EP) . |
| 0 484 071 A2 | 5/1992 | (EP) . |
| 0498 290 A1 | 8/1992 | (EP) . |
| 0 513 917 A1 | 11/1992 | (EP) . |
| 0 530 994 A1 | 3/1993 | (EP) . |
| WO 90/14825 | 12/1990 | (WO) . |
| WO 91/09849 | 7/1991 | (WO) . |
| WO 91/17159 | 11/1991 | (WO) . |
| WO 92/00952 | 1/1992 | (WO) . |
| WO 92/00979 | 1/1992 | (WO) . |
| WO 92/14743 | 9/1992 | (WO) . |
| WO 92/15309 | 9/1992 | (WO) . |
| 92/15309 * | 9/1992 | (WO) .................. A61K/31/505 |
| WO 93/02044 | 2/1993 | (WO) . |
| WO93/23021 | 11/1993 | (WO) . |

OTHER PUBLICATIONS

Field's Virology, Field et al Ed, Lippincott–Raven Pub., Philadelphia PA, p. 448, 1996.*

Proc. Natl. Acad. USA vol. 88, pp 6863–6867, Aug. 1991 Medical Sciences Goldman et al "Pyridinone derivatives: Specific human immunodeficiency virus type 1 reverse transcriptase inhibitors with antiviral activity".

Proc. Natl. Acad. Sci. USA vol. 88, pp. 9878–9882, Nov. 1991 Medical Sciences Shih et al "Chimeric human immunodeficiency virus type 1/type 2 reverse transcriptase display reversed sensitivity . . . ".

Proc. Natl. Acad. Sci. USA vol. 88, pp. 8806–8810 Oct. 1991 Medical Sciences Romero et al "Nonnucleoside reverse transcriptase inhibitors that potently and specifically block human immunodeficiency virus type . . . ".

Proc. Natl. Acad. Sci. USA vol. 88,, pp. 2356–2360, Mar. 1991 Medical Sciences Baba et al "Potent and Selective inhibition of human immunodeficiency virus type 1 (HIV–1) by 5–ethyl–6–phenylthiouracil . . . ".

No. Mech. Pathog. Infect. Dis No. 89, pp. 74–80 (1991) Jul. 1991 Zimmermann et al "Biochemical and Genetical Analysis of AZT–Resistant HIV–Mutants".

J. Virology, Sep. 1991, pp 4887–4892 vol. 65 No. 9 Nunberg et al "Viral Resistance to Human Immunodeficiency . . . ".

Antiviral Res. 17 (Suppl. 1) Mar. 1992, p. 46.

Antimicrob. Agents & Chemotherapy 36 (12) Dec. 1992 pp 2664–2669 Larder et al "3'–Azido–3'–Deoxythymidine Resistance Suppressed by a Mutation Conferring Human Immunodeficiency . . . Inhibitors".

Nature vol. 343 Feb. 1990 pp. 470–474 Pauwels et al "Potent and selective inhibition of HV–1 replication . . . ".

Aids Research & Human Retroviruses vol. 8 No. 2, 1992 pp. 119–134 De Clercq "HIV Inhibitors Targeted at the Reverse Transcriptase".

Proc. Natl. Acad. Sci. USA vol. 88, pp. 11241–11245 Dec. 1991 Microbiology Richman et al "Human immunodeficiency virus type 1 mutants resistant to nonnuceloside inhibitors . . . ".

Mol. Pharmacol. 43 (1) Jan. 1993, pp. 11–16 Mellors et al "A Single Conservative Amino Acid Substitution . . . ".

Science 253, Sep. 1991, pp. 1557–1559 Clair et al "Resistance to ddl and Sensitivity to AZT . . . Transcriptase".

Aids Research & Human Retroviruses vol. 8, No. 2, 1992 Grob et al "Nonnucleoside Inhibitors of HIV–1 Reverse Transcriptase: Nevirapine as a Prototype Drug".

(List continued on next page.)

* cited by examiner

*Primary Examiner*—Russell Travers
(74) *Attorney, Agent, or Firm*—Nixon & Vanderhye

(57) ABSTRACT

The use of a HIV-RT inhibitor to enhance the sensitivity to zidovudine of zidovudine-resistant HIV populations, the inhibitor being one which induces a mutation at the 181 or 184 position of the RT coding sequence.

4 Claims, No Drawings

OTHER PUBLICATIONS

Antimicrobial Agents & Chemotherapy, Feb. 1991 pp 305–308 Richman et al "BI–RG–587 is Active against Zidovudine . . . ".

Mol. Pharmacol. 41 (3) Mar. 1992, 446–451 Mellors et al "In Vitro Selection & Molecular Characterization . . . ".

Virology, 188 (2) Jun. 1992, pp. 900–904 De Vreese et al "Resistance of Human Immunodeficiency Virus . . . ".

Cammack et al 118 CA:73648g, 1992.*

Cammack et al 117 CA 103494C, 1992.*

Hoong et al 117 CA 192246P, 1992.*

THERAPEUTIC COMBINATIONS

This is a con application Ser. No. 08/221,009, filed Apr. 1, 1994, now abandoned. This is a continuation of PCT application No. PCT/GB93/00980, filed May 13, 1993.

The present invention relates to therapeutic combinations for the treatment of Human Immunodeficiency Virus (HIV) infections comprising zidovudine and an agent serving to enhance the antiviral activity of zidovudine against HIV populations otherwise resistant to attack by zidovudine.

Zidovudine, which has the chemical name 3'-azido-3'-deoxythymidine, is now well established as an important and useful chemotherapeutic agent for the treatment or prophylaxis of HIV-infections including related clinical conditions such as Acquired Immune Deficiency Syndrome (AIDS), AIDS-related complex (ARC) and also for the treatment of patients who have an asymptomatic HIV infection or who are anti-HIV antibody-positive.

Following the widespread clinical use of zidovudine in the therapy of such infections and conditions, it has been observed that in certain instances following prolonged treatment, the virus may develop a certain level of resistance to zidovudine and therefore a loss of sensitivity to the drug.

Other anti-HIV chemotherapeutic agents have been proposed and investigated, though very few of these agents have the combination of efficacy and safety possessed by zidovudine. Among these agents are various classes of non-nucleoside inhibitors of HIV reverse transcriptase which have been found to have potent anti-HIV activity in vitro. In contrast to nucleoside inhibitors these compounds do not need to be phosphorylated in vivo to exert their inhibitory effect but it has been found that their use rapidly induces resistance by the virus, i.e. loss of antiviral sensitivity to the compound by the virus. Other agents include antiviral nucleoside analogues containing an oxathiolane residue in place of the sugar residue for example nucleosides as described in European Patent Specification No. 382526 particularly (–)-2',3'-dideoxy-3'-thiacytidine, otherwise known as 3TC or lamivudine, and PCT Patent Specification No. WO 92/14743 particularly (–)-2'3'-dideoxy-5-fluoro-3'-thiacytidine otherwise known as FTC. These compounds may be prepared as described in the above relevant Patent Specification.

We have now discovered a solution to the problem encountered in anti-HIV therapy of the development of resistance to zidovudine by the virus. In particular, we have found that the development and maintenance of resistance by HIV populations can be reduced or prevented, i.e. the sensitivity of such populations to zidovudine can be enhanced, by treating the virus population with an inhibitor of HIV-reverse transcriptase (HIV-RT) which induces a mutation in the RT coding sequence (a) in which the tyrosine residue at position 181 is replaced by a cysteine residue; or (b) in which the methionine residue at position 184 is replaced by a valine or isoleucine residue; such an inhibitor will be referred to hereinafter as "a mutation-inducing HIV-RT inhibitor".

Examples of an HIV-RT inhibitor inducing a mutation of type (a) above include non-phosphorylated HIV-RT inhibitors, ie. inhibitors which are not required to be phosphorylated in vivo to be able to effect inhibition of HIV-RT.

Examples of an HIV-RT inhibitor inducing a mutation of type (b) above include oxathiolane nucleosides of the above types.

According to the present invention therefore we provide:

(a) a mutation-inducing HIV-RT inhibitor for use in enhancing or maintaining the antiviral sensitivity of an HIV population to zidovudine or a physiologically functional derivative thereof;

b) a therapeutic combination for the treatment or prophylaxis of HIV infections, especially zidovudine-resistant HIV infections, which comprises zidovudine or a physiologically functional derivative thereof, and a mutation-inducing HIV-RT inhibitor, whereby the antiviral sensitivity of a HIV population to zidovudine is enhanced or maintained by the said inhibitor;

(c) a method of enhancing or maintaining the antiviral sensitivity of an HIV population to zidovudine or a physiologically functional derivative thereof which comprises contacting said population with an effective amount of a mutation-inducing HIV-RT inhibitor;

(d) a method of treating a subject (e.g. a human) having an HIV infection resistant to zidovudine which comprises administering to the subject a combination of zidovudine or a physiologically functional derivative thereof and a mutation-inducing HIV-RT inhibitor;

(e) a mutation-inducing HIV-RT inhibitor for use in HIV therapy against HIV infections which are resistant to zidovudine;

(f) a method of increasing the sensitivity of a HIV population resistant to zidovudine or a physiologically functional derivative thereof comprising treating the virus with a mutation-inducing HIV-RT inhibitor.

It will be appreciated that the enhancement or maintenance of sensitivity to zidovudine of an HIV population in a patient can be readily determined in conventional manner, for example by observation of the relative clinical efficacy of the drug and/or by analytical determination of the levels of the virus or markers thereof in samples of appropriate biological materials (e.g. plasma) from the patient and/or by the determination of antiviral sensitivity in vitro in cell cultures of virus obtained from patients.

We have carried out in vitro experiments in which an HIV-1 population containing four mutations in the HIV-RT which confer zidovudine resistance was exposed in cell culture to increasing concentrations of a non-phosphorylated HIV-RT inhibitor represented by the compound known as "Chloro-TIBO", i.e. 9-chloro-4,5,6,7-tetrahydro-5-methyl-6-(3-methyl-2-butenyl)-S-imidazo[4,5,i-jk][1,4]benzodiazepine-2(1H)-thione. The virus became gradually more resistant to Chloro-TIBO and after five passages the 50% inhibitory concentration ($IC_{50}$) for the compound against the virus had increased by more than fifty-fold, i.e. antiviral sensitivity to Chloro-TIBO had decreased. In contrast the sensitivity of the virus population to zidovudine had simultaneously increased about twenty fold, the $IC_{50}$ value for zidovudine decreasing from about 2 $\mu$M to less than 0.1 $\mu$M. It has been discovered through similar in vitro passage experiments that HIV can acquire rapid resistance to oxathialane nucleosides such as FTC and 3TC. Thus, the introduction of the M184 to V mutation into a zidovudine-resistant HIV strain (HIVRTMC), resulted in an increase in resistance to FTC ($IC_{50}$ values increased from 0.64 $\mu$M to >500 $\mu$M), whereas the virus became less resistant to zidovudine ($IC_{50}$ values fell from 1.26 $\mu$M to 0.17 $\mu$M). When the resistance mutation, Y181 to C, together with M184 to V, were introduced into this zidovudine-resistant virus, there was an even more pronounced effect on the enhancement of zidovudine sensitivity. The resulting mutant virus strain was now co-resistant to the oxathialane nucleosides and non-phosphorylated HIV-RT inhibitors, but had become completely sensitive to zidovudine ($IC_{50}$ values for zidovudine fell from 1.26 to 0.04).

In accordance with the present invention, a mutation-inducing HIV-RT inhibitor may be used to enhance the antiviral sensitivity of a zidovudine-resistant HIV population to zidovudine or alternatively to maintain the antiviral sensitivity of a HIV population in which zidovudine-resistance has not been induced.

Examples of non-phosphorylated HIV-RT inhibitors which may be employed in conjunction with the invention include:

a) tetrahydro-imidazo[4,5,1-jk][1,4]-benzodiazepin-2 (1H)-ones and -thiones (the so-called "TIBO" derivatives) for example as described by Pauwels et al (1990) Nature, 343, 470–474, and in European Patent Specification No. 384522.

A particularly preferred TIBO derivative for use in accordance with the invention is "Chloro-TIBO" (R-82913) referred to above.

b) dipyridodiazepinones for example as described by Merluzzi et al (1990) Science, 250, 1411–1413 and in European Patent Specification No. 429987.

A particular example of this class of compounds is the compound known as nevirapine (BI-RG-587), i.e. 11-cyclopropyl-5-,11-dihydro-4-methyl-6H-dipyrido [3,2-6:2',3'-e][1,4]diazepin-6-one.

c) pyridinones (the so-called "L-drugs") for example as described by Goldman et al (1991) Proc. Nat. Acad. Sci, 88, 6863–6867 and in European Patent Specification No.462800.

A particular example of this class of compounds is L-697,639, i.e. 3-[[(4,7-dimethyl-2-benzoxazolyl) methyl]amino]-6-ethyl-6-methyl-2(1H)pyridinone.

d) bis(heteroaryl)piperazines (the so-called "BHAPS") as described for example by Romero et al (1991) Proc. Nat. Acad. Sci., 8806–8810 and in International Patent Specification No. WO 91/09849.

A particular example of this class of compounds is U-87201, namely 1-[3-(ethylamino)-2-pyridinyl]-4-[(5-methoxy-1H-indol-2-yl)carbonyl]-piperazine.

e) 5-ethyl-6-(phenylthio)uracil derivatives (the so-called "HEPT compounds") as described for example by Baba et al, Proc. Nat. Acad. Sci, (1991) 88, 2356–2360 and in European Patent Specification No. 420763.

f) quinazoline derivatives for example as described in European Patent Specification No. 530994.

g) anilinophenylacetamide derivatives for example as described in Proc. Natl. Acad. Sci. Vol 90, 1711–15, 1993

As an alternative to the non-phosphorylated HIV-RT inhibitor employed in accordance with the invention as described above, it is possible to use a HIV-RT inhibitor which induces a mutation in the RT coding sequence in which a methionine residue at position 184 is replaced by a valine or isoleucine residue (a "184 mutation HIV-RT inhibitor"). Such HIV-RT inhibitors may therefore be used in place of, or in addition to, the non-phosphorylated HIV-RT inhibitor as previously described. Examples of the 184 mutation HIV-RT inhibitors include antiviral nucleoside analogues containing an oxathiolane residue in place of the sugar residue for example nucleosides as described in European Patent Specification No. 382526 particularly (−)-2',3'-dideoxy-3'-thiacytidine, otherwise known at 3TC or lamivudine, and PCT Patent Specification No. WO 92/14743 particularly (−)-2'3'-dideoxy-5-fluoro-3'-thiacytidine otherwise known as FTC. These compounds may be prepared as described in the above relevant Patent Specification.

An especially preferred embodiment of the present invention comprises the use of a non-phosphorylated HIV-RT inhibitor and a 184 mutation HIV-RT inhibitor such as lamivudine or FTC together with zidovudine. The use in combination of the two types of HIV-RT inhibitor results in a very significant effect in reducing or preventing the development and maintenance by HIV populations of resistance to zidovudine.

By "physiologically functional derivative" of zidovudine is meant a pharmaceutically acceptable salt, ester or salt of an ester of zidovudine, or any other compound which upon administration to the recipient is capable of providing (directly or indirectly) zidovudine or an active metabolite or residue thereof.

Preferred esters according to the invention include carboxylic acid esters in which the non-carbonyl moiety of the ester grouping is selected from straight or branched chain alkyl e.g. n-propyl, t-butyl, n-butyl, alkoxyalkyl (e.g. methoxymethyl), aralkyl (e.g. benzyl), aryloxyalkyl (e.g. phenoxymethyl), and aryl (e.g. phenyl); sulfonate esters such as alkyl- or aralkylsulfonyl (e.g. methanesulfonyl); amino acid esters (e.g. L-valyl or L-isoleucyl); dicarboxylic acid esters (e.g., hemisuccinate); and mono-, di- or triphosphate esters. The phosphate esters may be further esterified by, for example, a $C_{1-20}$ alcohol or reactive derivative thereof, or by a 2,3-di($C_{6-24}$)acyl glycerol.

Any alkyl moiety present in such esters advantageously contains 1 to 18 carbon atoms, particularly 1 to 4 carbon atoms. Any aryl moiety present in such esters advantageously comprises a phenyl group optionally substituted, e.g. by halogen, $C_{1-4}$ alkyl, $C_{1-4}$ alkoxy or nitro.

Examples of pharmaceutically acceptable salts include base salts, e.g. derived from an appropriate base, such as alkali metal (e.g. sodium), alkaline earth metal (e.g. magnesium) salts, ammonium and $NX_4^+$(wherein X is $C_{1-4}$ alkyl). Pharmaceutically acceptable acid addition salts include salts of organic carboxylic acids such as acetic, lactic, tartaric, malic, isethionic, lactobionic and succinic acids; organic sulfonic acids such as methanesulfonic, ethanesulfonic, benzenesulfonic and p-toluenesulfonic acids and inorganic acids such as hydrochloric, sulfuric, phosphoric and sulfamic acids.

Examples of viral infections and associated clinical conditions which may be treated or prevented in accordance with the invention, include human retroviral infections such as HIV, e.g. HIV-1 or HIV-2, and human T-cell lymphotropic virus (HTLV), e.g. HTLV-I or HTLV-II infections. The combinations of the present invention are especially useful for the treatment of AIDS and related clinical conditions such as AIDS-related complex (ARC), progressive generalized lymphadenopathy (PGL), AIDS-related neurological conditions, such as multiple sclerosis or tropical paraparesis, anti-HIV antibody-positive and HIV-positive conditions such as thrombocytopenic purpura. The combinations of the present invention may also be used in the treatment of psoriasis. The combinations of the present invention have been found to be particularly applicable to the treatment of asymptomatic infections or diseases caused by or associated with HIV.

It will be appreciated that in accordance with the present invention the components of the combinations may be administered simultaneously, concurrently or sequentially. In the latter case, however, the components are administered within a sufficiently short interval to ensure that an enhancement of the antiviral sensitivity of an HIV population to zidovudine is achieved.

An advantage of the combinations of the present invention is that it enables one to treat subjects having a zidovudine-resistant HIV infection who would otherwise be precluded from such treatment with the drug.

Zidovudine and/or the mutation-inducing HIV-RT inhibitor may employed in accordance with the invention together with other therapeutic agents for the treatment of the above infections or conditions. Examples of such further therapeutic agents include agents that are effective for the treatment of HIV infections or associated conditions, such as 2',3'-dideoxynucleosides, e.g. 2',3'-dideoxycytidine, 2',3'-dideoxyadenosine and 2',3'-dideoxyinosine, carbovir, 2',3'-didehydrothymidine, acyclic nucleosides (for example, acyclovir), protease inhibitors, such as RO 31-8959, oxathiolan nucleoside analogues, such as, cis-1-(2-hydroxymethyl)-1,3-oxathiolan-5-yl)cytosine (3TC), interferons, such as a-interferon, renal excretion inhibitors, such as probenicid, nucleoside transport inhibitors, such as dipyridamole, as well as immunomodulators, such as interleukin II, granulocyte macrophage colony stimulating factors, and erythropoetin, phosphonoformic acid, soluble $CD_4$ and genetically engineered derivatives thereof. The component compounds of such combination therapy may be administered simultaneously, in either separate or combined formulations, or at different times, for example sequentially, such that a combined effect is achieved.

The compounds employed in accordance with the present invention may be administered to a mammal in a conventional manner. As indicated above, the components of the above combinations may be administered simultaneously (e.g., in a unitary pharmaceutical formulation) or separately (e.g., in separate pharmaceutical formulations). In general, the combinations may be administered by the topical, oral, rectal or parenteral (e.g., intravenous, subcutaneous or intramuscular) routes. It will be appreciated that the route may vary with, for example, the severity of the condition to the treated and the identity of the recipient.

Thus the optimum molar ratio of the zidovudine (or a physiologically functional derivative thereof) to the mutation-inducing HIV-RT inhibitor for use according to this invention is from 10:1 to 1:10, preferably from 1:1 to 1:5, and most preferably 1:3.

Hereafter the components of the combination may be referred to as "active ingredients".

The dosages of the compounds will depend on the condition being treated and other clinical factors such as the weight and condition of the recipient and the route of administration of the components of the combinations. Examples of dose ranges and component ratios are as follows:

In general a suitable dose of zidovudine (or a physiologically functional derivative thereof) will be in the range of 3 to 120 mg per kilogram body weight of the recipient per day, preferably in the range of 6 to 90 mg per kilogram body weight per day and most preferably in the range 10 to 30 mg per kilogram body weight per day. The desired dose is preferably presented as two, three, four, five, six or more sub-doses administered at appropriate intervals throughout the day. These sub-doses may be administered in unit dose forms, for example, containing a total of 10 to 1500 mg, preferably 20 to 1000 mg, and most preferably 50 to 700 mg of active ingredients per unit dose form.

With regard to the non-phosphorylated HIV-RT inhibitor, the dosage will vary depending on the particular inhibitor employed in addition to the other factors referred to above. However, in general, a daily dosage of 0.1 to 100 mg/kg for example 1 to 50 mg/kg may be employed. Preferred daily dosages for the specific compounds or groups of compounds preferred to above are 0.01 to 20, preferably 0.1 to 5 mg/kg for Chloro-TIBO, 0.5 mg to 1 g /day for nevirapine, 1 to 20 mg/kg for L-697,639, 0.1 to 500 mg/kg for U-87201 and 1 to 100, preferably 5 to 50 mg/kg for the HEPT compounds.

With regard to the above 184 mutation HIV-RT inhibitors such as the antiviral oxathiolane nucleosides, daily doses for the compounds described in European Patent Specification No. 382526 include 1 to 750 mg/kg, preferably 3 to 120 mg/kg especially 6 to 90 mg/kg. Daily doses for the compounds described in PCT Patent Specification No. WO 92/14743 include 0.1 to 100 mg/kg, preferably 1 to 50mg/kg especially 1 to 20 mg/kg.

While it is possible for the active ingredients to be administered alone it is preferable to present them as pharmaceutical formulations. Pharmaceutical formulations of the present invention comprise a combination according to the invention together with one or more pharmaceutically acceptable carriers or excipients and optionally other therapeutic agents. When the individual components of the combination are administered separately they are generally each presented as a pharmaceutical formulation. The references hereinafter to formulations refer unless otherwise stated to formulations containing either the combination or a component thereof. Formulations include those suitable for oral, rectal, nasal, topical (including transdermal, buccal and sublingual), vaginal or parenteral (including subcutaneous, intramuscular, intravenous and intradermal) administration. The formulations may conveniently be presented in unit dosage form and may be prepared by any methods well known in the art of pharmacy. Such methods include the step of bringing into association the active ingredients with the carrier which constitutes one or more accessory ingredients.

In general, the formulations are prepared by uniformly and intimately bringing into association the active ingredients with liquid carriers or finely divided solid carriers or both, and then if necessary shaping the product.

Formulations of the present invention suitable for oral administration may be presented as discrete units such as capsules, cachets or tablets each containing a predetermined amount of the active ingredients; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredients in a free-flowing form such as a powder or granules, optionally mixed with a binder (e.g. povidone, gelatin, hydroxypropylmethyl cellulose), lubricant, inert diluent, preservative, disintegrant (e.g. sodium starch glycollate, cross-linked povidone, cross-linked sodium carboxymethyl cellulose) surface-active or dispersing agent. Molded tablets may be made by molding a mixture of the powdered compound moistened with an inert liquid diluent in a suitable machine. The tablets may optionally be coated or scored and may be formulated so as to provide slow or controlled release of the active ingredients therein using, for example, hydroxypropylmethyl cellulose in varying proportions to provide the desired release profile. Tablets may optionally be provided with an enteric coating, to provide release in parts of the gut other than the stomach.

Formulations suitable for topical administration in the mouth include lozenges comprising the active ingredients in a flavored base, usually sucrose and acacia or tragacanth; pastilles comprising the active ingredient in an inert basis such as gelatin and glycerin, or sucrose and acacia, and mouthwashes comprising the active ingredient in a suitable liquid carrier. Formulations for rectal administration may be presented as a suppository with a suitable base comprising, for example, cocoa butter or a salicylate.

Topical administration may also be by means of a transdermal iontophoretic device.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and nonaqueous isotonic sterile injection solutions which may contain anti-oxidants, buffers, bacteriostats and solutes which render the formulation isotonic with the blood of the intended recipient; and aqueous and non-aqueous sterile suspensions which may include suspending agents and thickening agents; and liposomes or other microparticulate systems which are designed to target the compound to blood components or one or more organs. The formulations may be presented in unit-dose or multi-dose sealed containers, for example, ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or daily subdose of the active ingredients, as hereinbefore recited, or an appropriate fraction thereof.

It should be understood that in addition to the ingredients particularly mentioned above the formulations of this invention may include other agents conventional in the art having regard to the type of formulation in question, for example, those suitable for oral administration may include such further agents as sweeteners, thickeners and flavoring agents.

The compounds of the combination of the present invention may be obtained in conventional manner. Zidovudine can be prepared, for example, as described in U.S. Pat. No. 4,724,232, incorporated herein by reference. Zidovudine can also be obtained from Aldrich Chemical Co., Milwaukee, Wis. 53233, USA.

The mutation-inducing HIV-RT inhibitors can be prepared in accordance with the processes described in the above-references relating to such inhibitors.

The following examples are intended for illustration only and are not intended to limit the scope of the invention in any way. "Active ingredient" denotes zidovudine and/or a non-phosphorylated HIV-RT inhibitor.

EXAMPLE 1

Tablet Formulation

The following formulations A, B and C are prepared by wet granulation of the ingredients with a solution of povidone, followed by addition of magnesium stearate and compression.

| Formulation A | mg/tablet |
|---|---|
| Active Ingredient | 250 |
| Lactose B. P. | 210 |
| Povidone B. P. | 15 |
| Sodium Starch Glycollate | 20 |
| Magnesium Stearate | 5 |
| | 500 |

| Formulation B | mg/tablet |
|---|---|
| Active Ingredient | 250 |
| Lactose B. P. | 150 |
| Avicel PH 101 | 60 |
| Povidone B. P. | 15 |
| Sodium Starch Glycollate | 20 |
| Magnesium Stearate | 5 |
| | 500 |

| Formulation C | mg/tablet |
|---|---|
| Active Ingredient | 250 |
| Lactose B. P. | 200 |
| Starch | 50 |
| Povidone | 5 |
| Magnesium Stearate | 4 |
| | 359 |

The following formulations, D and E, are prepared by direct compression of the admixed ingredients. The lactose in formulation E is of the direct compression type (Dairy Crest - "Zeparox").

| Formulation D | mg/tablet |
|---|---|
| Active Ingredient | 250 |
| Pregelatinized Starch NF15 | 150 |
| | 400 |

| Formulation E | mg/tablet |
|---|---|
| Active Ingredient | 250 |
| Lactose B. P. | 150 |
| Avicel | 100 |
| | 500 |

Formulation F (Controlled Release Formulation)

The formulation is prepared by wet granulation of the ingredients with a solution of povidone followed by the addition of magnesium stearate and compression.

| | mg/tablet |
|---|---|
| Active Ingredient | 500 |
| Hydroxypropylmethylcellulose (Methocel K4M Premium) | 112 |
| Lactose B. P. | 53 |
| Povidone B. P. | 28 |
| Magnesium Stearate | 7 |
| | 700 |

Drug release takes place over a period of about 6–8 hours and is complete after 12 hours.

EXAMPLE 2

Capsule Formulations

Formulation A

A capsule formulation is prepared by admixing the ingredients of formulation D in Example 1 above and filling into a two-part hard gelatin capsule. Formulation B (infra) is prepared in a similar manner.

| Formulation B | mg/capsule |
|---|---|
| Active Ingredient | 250 |
| Lactose B. P. | 143 |
| Sodium Starch Glycollate | 25 |
| Magnesium Stearate | 2 |
| | 420 |

| Formulation C | mg/capsule |
|---|---|
| Active Ingredient | 250 |
| Macrogel 4000 B. P. | 350 |
| | 600 |

Capsules of formulation C are prepared by melting the Macrogel 4000 B.P., dispersing the active ingredient in the melt and filling the melt into a two-part hard gelatin capsule.

| Formulation D | mg/capsule |
|---|---|
| Active Ingredient | 250 |
| Lecithin | 100 |
| Arachis Oil | 100 |
| | 450 |

Capsules of formulation D are prepared by dispersing the active ingredient in the lecithin and arachis oil and filling the dispersion into soft, elastic gelatin capsules.

Formulation E (Controlled Release Capsule)

The following controlled release capsule formulation is prepared by extruding ingredients a, b, and c using an extruder, followed by spheronization of the extrudate and drying. The dried pellets are then coated with release-controlling membrane (d) and filled into a two-piece, hard gelatin capsule.

| | mg/capsule |
|---|---|
| (a) Active Ingredient | 250 |
| (b) Microcrystalline Cellulose | 125 |
| (c) Lactose B. P. | 125 |
| (d) Ethyl Cellulose | 13 |
| | 513 |

EXAMPLE 3

Injectable Formulation

| Formulation A | mg |
|---|---|
| Active Ingredient | 200 |
| Hydrochloric Acid Solution 0.1 M or Sodium Hydroxide Solution 0.1 M q.s. to pH | 4.0 to 7.0 |
| Sterile water q.s. to | 10 ml |

The active ingredient is dissolved in most of the water (35°–40° C.) and the pH adjusted to between 4.0 and 7.0 with the hydrochloric acid or the sodium hydroxide as appropriate. The batch is then made up to volume with the water and filtered through a sterile micropore filter into a sterile 10 ml amber glass vial (type 1) and sealed with sterile closures and overseals.

| Formulation B | |
|---|---|
| Active Ingredient | 125 mg |
| Sterile, Pyrogen-free, pH 7 Phosphate Buffer, q.s. to | 25 ml |

EXAMPLE 4

Intramuscular Injection

| | |
|---|---|
| Active Ingredient | 200 mg |
| Benzyl Alcohol | 0.10 g |
| Glycofurol 75 | 1.45 g |
| Water for injection q.s. to | 3.00 ml |

The active ingredient is dissolved in the glycofurol. The benzyl alcohol is then added and dissolved, and water added to 3 ml. The mixture is then filtered through a sterile micropore filter and sealed in sterile 3 ml amber glass vials (type 1).

EXAMPLE 5

Syrup

| | |
|---|---|
| Active Ingredient | 250 mg |
| Sorbitol Solution | 1.50 g |
| Glycerol | 2.00 g |

-continued

| | |
|---|---|
| Sodium Benzoate | 0.005 g |
| Flavor, Peach 17.42.3169 | 0.0125 ml |
| Purified Water q.s. to | 5.00 ml |

The active ingredient is dissolved in a mixture of the glycerol and most of the purified water. An aqueous solution of the sodium benzoate is then added to the solution, followed by addition of the sorbital solution and finally the flavor. The volume is made up with purified water and mixed well.

EXAMPLE 6

Suppository

| | mg/capsule suppository |
|---|---|
| Active Ingredient | 250 |
| Hard Fat, B. P. (Witepsol H15-Dynamit Nobel) | 1770 |
| | 2020 |

One-fifth of the Witepsol H15 is melted in a steam-jacketed pan at 45° C. maximum. The active ingredient is sifted through a 2001M sieve and added to the molten base with mixing, using a Silverson fitted with a cutting head, until a smooth dispersion is achieved. Maintaining the mixture at 45° C., the remaining Witepsol H15 is added to the suspension and stirred to ensure a homogenous mix. The entire suspension is passed through a 2501 m stainless steel screen and, with continuous stirring, is allowed to cool to 40° C. At a temperature of 38° C. to 40° C., 2.02 g of the mixture is filled into suitable, 2 ml plastic molds. The suppositories are allowed to cool to room temperature.

EXAMPLE 7

Pessaries

| | mg/pessary |
|---|---|
| Active Ingredient | 250 |
| Anhydrate Dextrose | 380 |
| Potato Starch | 363 |
| Magnesium Stearate | 7 |
| | 1000 |

The above ingredients are mixed directly and pessaries prepared by direct compression of the resulting mixture.

What is claimed is:

1. A method of treating HIV infections in a subject in need of such therapy by maintaining the antiviral sensitivity of a patient' HIV population to zidovudine or physiologically functional derivative thereof by contracting said viral population with an effective amount of an HIV-RT inhibitor which induces a mutation in the RT coding sequence (a) wherein the tyrosine residue at position 181 of HIV-RT is replaced by a cysteine residue or (b) wherein the methionine residue at position 184 of HIV-RT is replaced by valine or isoleucine residue comprising the steps of
    (a) identifying a subject having an HIV infection resistant to zidovudine,
    (b) administering to that patient (−)-2',3'-dideoxy-5-fluoro3'-thiacytidine and/or (−)-2',3'thiacytidine,
    (c) upon resistance development by said patients HIV infection to the therapy in step (b) administer zidovudine to said patient, and optionally
    (d) upon resistance development by said patients HIV infection to the therapy in step (c) administer to that patient (−)-2',3'-dideocy-5-fluoro-3'-thiacytidine and/or (−)-2',3'-dideoxy-3'-thiacytidine, and
    (e) repeat steps (c) and (d) as resistance develops to the currently employed medicament.

2. A method as claimed in claim 1 wherein the compound administered in step (b) is (−)-2',3'-dideoxythiacytidine.

3. A method as claimed in claim 1 wherein the compound administered in step (b) is (−)-2',3'-dideoxy-5-fluoro-3'-thiacytidine.

4. A method of treating HIV infections in a subject in need of such therapy by maintaining the antiviral sensitivity of a patient' HIV population to zidovudine or physiologically functional derivative thereof by contracting said viral population with an effective amount of an HIV-RT inhibitor which induces a mutation in the RT coding sequence (a) wherein the tyrosine residue at position 181 of HIV-RT is replaced by a cysteine residue or (b) wherein the methionine residue at position 184 of HIV-RT is replaced by valine or isoleucine residue comprising the steps of
    (a) identifying a subject having an HIV infection resistant to zidovudine
    (b) administering to that patient (−)-2',3'-dideoxy-5-fluoro-3'-thiacytidine and/or (−)-2',3'thiacytidine,
    (c) upon resistance development by said patients HIV infection to the therapy in step (b) administer zidovudine to said patient,
    (d) upon resistance development by said patients HIV infection to the therapy in step (c) administer to that patient (−)-2',3'-dideocy-5-fluoro-3'-thiacytidine and/or (−)-2',3'-dideoxy-3'-thiacytidine, and
    (e) repeat steps (c) and (d) as resistance develops to the currently employed medicament.

* * * * *

UNITED STATES PATENT AND TRADEMARK OFFICE
CERTIFICATE OF CORRECTION

PATENT NO.    : 6,177,435 B1
DATED         : January 23, 2001
INVENTOR(S)   : Larder et al.

It is certified that error appears in the above-identified patent and that said Letters Patent is hereby corrected as shown below:

<u>Column 12,</u>
Line 15, insert a hyphen (-) between fluoro and 3' -- fluoro-3' --;
Lines 22 and 50, delete "dideocy" and insert -- dideoxy --.

Signed and Sealed this

First Day of January, 2002

Attest:

JAMES E. ROGAN
*Director of the United States Patent and Trademark Office*

*Attesting Officer*